(12) United States Patent
    Igarashi

(10) Patent No.:    US 12,686,883 B2
(45) Date of Patent:        Jul. 21, 2026

(54) SAMPLING METHOD

(71) Applicant: Terumo Kabushiki Kaisha, Tokyo (JP)

(72) Inventor: Masatsugu Igarashi, Kanagawa (JP)

(73) Assignee: Terumo Kabushiki Kaisha (JP)

( * ) Notice: Subject to any disclaimer, the term of this patent is extended or adjusted under 35 U.S.C. 154(b) by 602 days.

(21) Appl. No.: 18/205,302

(22) Filed: Jun. 2, 2023

(65) Prior Publication Data

US 2023/0313262 A1    Oct. 5, 2023

Related U.S. Application Data

(63) Continuation of application No. PCT/JP2022/003051, filed on Jan. 27, 2022.

(30) Foreign Application Priority Data

Feb. 2, 2021    (JP) ................................. 2021-014846

(51) Int. Cl.
    *C12Q 1/24*        (2006.01)
    *C12M 1/00*        (2006.01)
    *C12M 1/34*        (2006.01)
(52) U.S. Cl.
    CPC .............. *C12Q 1/24* (2013.01); *C12M 29/00* (2013.01); *C12M 29/04* (2013.01); *C12M 39/00* (2013.01); *C12M 41/34* (2013.01); *C12M 41/46* (2013.01)
(58) Field of Classification Search
    CPC ......... C12Q 1/24; C12M 29/00; C12M 29/04; C12M 39/00; C12M 41/34; C12M 41/46; C12M 41/32; C12M 33/00; C12M 41/48; G01N 1/00; C12N 1/00; C12N 5/00
    See application file for complete search history.

(56) References Cited

U.S. PATENT DOCUMENTS

| | | | |
|---|---|---|---|
| 9,442,047 B2 | 9/2016 | Biksacky | |
| 2011/0275056 A1* | 11/2011 | Antwiler | ................ C12M 41/32 |
| | | | 435/287.1 |
| 2014/0033834 A1 | 2/2014 | Biksacky | |
| 2014/0087413 A1 | 3/2014 | Newbold et al. | |

(Continued)

FOREIGN PATENT DOCUMENTS

| | | |
|---|---|---|
| EP | 3556840 A1 | 10/2019 |
| JP | 2016508229 A | 3/2016 |

OTHER PUBLICATIONS

Written Opinion of the International Searching Authority issued in the corresponding PCT Application No. PCT/JP2022/003051; mailed on Mar. 8, 2022 (total 6 pages).

(Continued)

*Primary Examiner* — John McGuirk
(74) *Attorney, Agent, or Firm* — Harness, Dickey & Pierce, P.L.C.

(57)    ABSTRACT

A sampling method includes: a sampling step of circulating a sample from a cell culture device to a sampling channel and measuring concentrations of predetermined components in the sample by a second sensor and a gas concentration sensor; a cleaning step of circulating a cleaning liquid through the sampling channel to circulate the cleaning liquid through the second sensor and the gas concentration sensor after the sampling step; and an air introduction step of replacing the cleaning liquid remaining in the gas concentration sensor with air after the cleaning step.

20 Claims, 9 Drawing Sheets

(56)      References Cited

U.S. PATENT DOCUMENTS

2015/0355135  A1*  12/2015  Gover ..................... B01L 99/00
                                                            205/775
2019/0086391  A1    3/2019  Nahmias et al.

OTHER PUBLICATIONS

European Search Report dated May 27, 2024, issued in corresponding EP Application No. 22749601.5.
European Written Opinion dated May 27, 2024, issued in corresponding EP Application No. 22749601.5.
Office Action issued in corresponding Japanese Application No. 2022-579494, dated Nov. 11, 2025 (4 pgs).
International Search Report dated Mar. 8, 2022, issued in corresponding PCT Application No. PCT/JP2022/003051 with English translation (5 pages).

* cited by examiner

SAMPLING METHOD

CROSS-REFERENCE TO RELATED APPLICATIONS

The present application is a continuation application of the International Patent Application No. PCT/JP2022/003051 filed on Jan. 27, 2022, which designated the U.S. and claims the benefit of priority from Japanese Patent Application No. JP2021-014846 filed on Feb. 2, 2021. The entire disclosures of the above-identified applications are incorporated herein by reference.

FIELD

The present disclosure relates to a sampling method.

BACKGROUND

A sampling system includes a sampling channel and an introduction path. The sampling channel may include a biosensor and a gas concentration sensor provided to be in contact with a sample moving through the sampling channel. The introduction path is configured to introduce a cleaning liquid to the sampling channel upstream of the biosensor and the gas concentration sensor. A method for using the sampling system may include a sampling step and a cleaning step. The sample step may include circulating the sample in the sampling channel bring the sample into contact with the biosensor and/or the gas concentration sensor. The cleaning step may include introducing a cleaning liquid from the introduction path into the sampling channel. The cleaning liquid may be used to remove sample attached to the biosensor so as to prevent deterioration of a catalyst of the biosensor.

When the cleaning step is completed, the cleaning liquid may remain inside the gas concentration sensor. When the gas concentration sensor has a relatively large capacity, the cleaning liquid may be with mixed the sample within the gas concentration sensor during the sampling step, which can decrease the measurement accuracy of the gas concentration sensor.

The present disclosure provides a sampling method that is capable of removing samples attached to biosensors and also of improving the accuracy of gas concentration sensors.

SUMMARY

In at least one example embodiment, a sampling method uses a sampling system. The sampling system includes a sampling channel configured to receive a liquid sample from a cell culture device. The sampling channel includes a biosensor and a gas concentration sensor provided in the sampling channel so as to be in contact with the sample. The sampling method includes a sampling step, a cleaning step, and an air introduction step. The sampling step includes circulating the sample from the cell culture device to the sampling channel and measuring concentrations of predetermined components in the sample using the biosensor and the gas concentration sensor. The cleaning step includes, after the sampling step, circulating a cleaning liquid through the sampling channel so as to circulate the cleaning liquid through the biosensor and the gas concentration sensor. The air introduction step includes, after the cleaning step, replacing the cleaning liquid remaining in the gas concentration sensor with air. The sampling method may include performing the sampling step two or more times, and the second and subsequent sampling steps may be performed after the air introduction step.

In at least one example embodiment, the cleaning step may be performed after the sampling step so that any amount of sample attached to the biosensor during the sampling step can be removed by the cleaning liquid in the cleaning step. In the air introduction step may be performed after the cleaning step so that any amount of the cleaning liquid remaining in the gas concentration sensor may be replaced with air such that the cleaning liquid is not mixed with the sample, for example inside the gas concentration sensor, in subsequent sampling steps, improving the accuracy of the gas concentration sensor.

BRIEF DESCRIPTION OF DRAWINGS

FIG. 1 is a schematic illustrating a sampling system in accordance with at least one example embodiment of the present disclosure.

FIG. 5 is a schematic illustrating a first operation of the sampling method illustrated in FIGS. 3 and 4 in accordance with at least one example embodiment of the present disclosure.

FIG. 6 is a schematic illustrating a second operation of the sampling method illustrated in FIGS. 3 and 4 in accordance with at least one example embodiment of the present disclosure.

FIG. 8 is a schematic illustrating a fourth operation of the sampling method illustrated in FIGS. 3 and 4 in accordance with at least one example embodiment of the present disclosure.

FIG. 9 is a schematic illustrating a fifth operation of the sampling method illustrated in FIGS. 3 and 4 in accordance with at least one example embodiment of the present disclosure.

DETAILED DESCRIPTION

Figure 2:
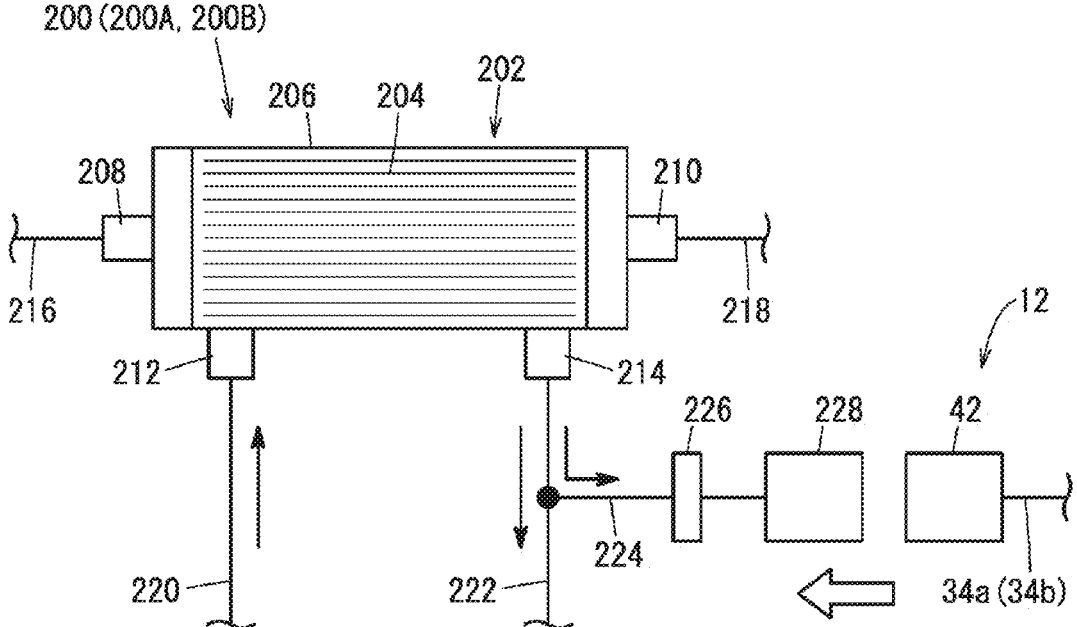
FIG. 2 is a schematic illustrating a main part of an example cell culture device in accordance with at least one example embodiment of the present disclosure.

Hereinafter, an example embodiment of a sampling method according to the present disclosure will be described with reference to the accompanying drawings.

Figure 1:
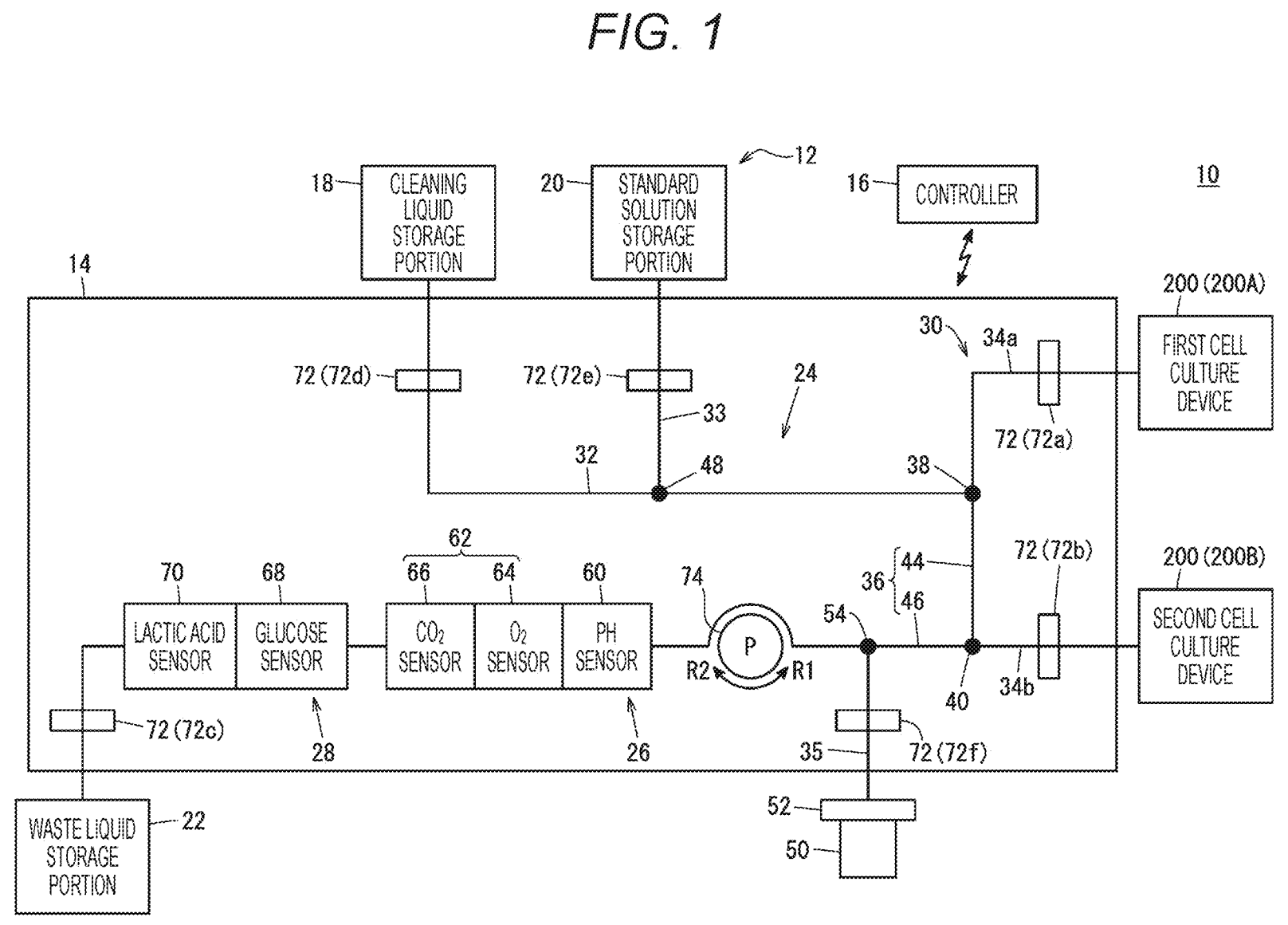

In at least one example embodiment, as illustrated in FIG. 1, a sampling system 10 is configured to collect liquid samples from a plurality of cell culture devices 200 and to measure concentrations of predetermined components in the samples. The sampling system 10 may include a sampling kit 12, a circuit control device 14 to which the sampling kit 12 is detachable, and a controller 16. The sampling kit 12 may be a disposable product. The circuit control device 14 may be a reusable product.

In at least one example embodiment, the plurality of cell culture devices 200 may include a first cell culture device 200A and a second cell culture device 200B. The first and second cell culture devices 200A, 200B may be connected to the sampling kit 12. As illustrated in FIG. 2, the cell culture device 200 may include a bioreactor 202 for culturing cells. The cells to be cultured may be separated from a biological tissue. For example, cells (e.g., T cells and/or the like) and/or stem cells (e.g., ES cells, iPS cells, mesenchymal stem cells, and/or the like) as contained in blood may be used.

The bioreactor 202 may be configured as a so-called hollow fiber bioreactor. The bioreactor 202 may include a number (e.g., plurality) of hollow fibers 204 and a cylindrical housing 206 configured to store the hollow fibers 204. A wall portion constituting the hollow fiber 204 may include a plurality of pores (not illustrated). Through the pores, an intra capillary (IC) region within a lumen of the hollow fiber 204 may communicated with an extra capillary (EC) region located outside the hollow fiber 204 in the housing 206. A diameter of the pores may be set to a size that allows passage of low molecular weight materials (for example, water, ions, oxygen, lactate, and/or the like) while blocking the passage of higher molecular weight materials (for example, cells and/or the like).

The housing 206 may be provided with an IC inlet port 208, an IC outlet port 210, an EC inlet port 212, and/or an EC outlet port 214. The IC inlet port 208 may be provided at one end of the housing 206. The IC inlet port 208 may be configured to introduce a liquid (e.g., a solution containing cells, a medium, or the like) guided from an IC inlet flow path 216 into the IC region of the bioreactor 202. The IC outlet port 210 may be provided at the other end of the housing 206. The IC outlet port 210 may direct a liquid flowing through the IC region of the bioreactor 202 to an IC outlet flow path 218.

The EC inlet port 212 and the EC outlet port 214 may be provided on an outer peripheral surface of the housing 206. The EC inlet port 212 may be configured to introduce a medium directed from an EC inlet flow path 220 into the EC region of the bioreactor 202. The EC outlet port 214 may be configured to direct a medium flowing through the EC region of the bioreactor 202 to an EC outlet flow path 222. As the medium, an appropriate medium may be selected according to cells of a living body. For example, a medium may be prepared by adding various amino acids, vitamins, serum, and/or the like to a basic solution. The basic solution may include balanced salt solution (BSS).

A connection line 224 for guiding the culture medium circulating in the EC region to the sampling kit 12 may be connected to the EC outlet flow path 222. The connection line 224 may be provided with a sterile filter 226 and a sampling connector 228. The sterile filter 226 may aseptically holds a portion of the cell culture device 200 closer to the EC outlet flow path 222 than the sterile filter 226. An introduction connector 42 of the sampling kit 12 may be detachable from the sampling connector 228.

In at least one example embodiment, the sampling system 10 may collect, as a sample, a culture medium circulating in the EC region of the cell culture device 200. However, the sample collected by the sampling system 10 is not limited to the medium circulating in the EC region and may be a medium or another liquid circulating in the IC region.

As illustrated in FIG. 1, the sampling kit 12 may include a cleaning liquid storage portion 18, a standard solution storage portion 20, a waste liquid storage portion 22, a connection circuit 24, a first sensor 26, and/or a second sensor 28.

The cleaning liquid storage portion 18, the standard solution storage portion 20, and/or the waste liquid storage portion 22 may be formed in a bag shape by using a flexible material made of a soft resin. The soft resin may include, for example, polyvinyl chloride and/or polyolefin. However, the cleaning liquid storage portion 18, the standard solution storage portion 20, and/or the waste liquid storage portion 22 can be appropriately changed as long as they can store liquid.

The cleaning liquid storage portion 18 may be configured to store a cleaning liquid. A buffer solution and/or physiological saline may be used as the cleaning liquid. The buffer solution may include, for example, phosphate buffered saline (PBS) and/or tris-buffered saline (TBS). The cleaning liquid is not limited to those described above.

The standard solution storage portion 20 may be configured to store a standard solution. The standard solution may be a liquid for calibrating the first sensor 26 and/or the second sensor 28. The standard solution may be a liquid in which a pH value, an $O_2$ value (oxygen concentration), a $CO_2$ value (carbon dioxide concentration), a glucose value (glucose concentration), and/or a lactic acid value (lactic acid concentration) are set to prescribed values.

The waste liquid storage portion 22 may be configured to store a waste liquid (e.g., used or unused portions of a sample, a cleaning liquid, and/or a standard solution) circulating in the connection circuit 24. The waste liquid storage portion 22 may include an empty bag in which no liquid is stored before the sampling kit 12 is used.

The connection circuit 24 may include a sampling channel 30 that collects a sample of a cell culture device 200, an introduction path 32 that guides a cleaning liquid to the sampling channel 30, a standard solution introduction path 33 that guides a standard solution to the introduction path 32, and/or an air introduction path 35 that guides air to the sampling channel 30. The sampling channel 30 may include a first sample introduction path 34a, a second sample introduction path 34b, and/or a sample flow path 36.

The first sample introduction path 34a may be configured to guide the sample (e.g., culture medium) of the first cell culture device 200A to the sample flow path 36. The introduction connector 42 attached to the sampling connector 228 of the first cell culture device 200A may be provided at one end of the first sample introduction path 34a (see FIG. 2). The other end of the first sample introduction path 34a may be connected to one end of the sample flow path 36. Hereinafter, a connection portion between the first sample introduction path 34a and the sample flow path 36 may be referred to as a first connection portion 38.

The second sample introduction path 34b may be configured to guide the sample (e.g., culture medium) of the second cell culture device 200B to the sample flow path 36. The introduction connector 42 attached to the sampling connector 228 of the second cell culture device 200B may be provided at one end of the second sample introduction path 34b (see FIG. 2). The other end of the second sample introduction path 34b may be connected to an intermediate portion of the sample flow path 36. Hereinafter, a connection portion between the second sample introduction path 34b and the sample flow path 36 may be referred to as a second connection portion 40.

The sample flow path 36 may include an intermediate flow path 44 that connects the first connection portion 38 and the second connection portion 40 to each other, and a sensor flow path 46 that connects the second connection portion 40 and the waste liquid storage portion 22 to each other.

One end of the introduction path 32 may be connected to the cleaning liquid storage portion 18. The other end of the introduction path 32 may be connected to the first connection portion 38. One end of the standard solution introduction path 33 may be connected to the standard solution storage portion 20. The other end of the standard solution introduction path 33 may be connected to an intermediate portion of the introduction path 32. Hereinafter, a connection portion between the introduction path 32 and the standard solution introduction path 33 may be referred to as a third connection portion 48.

An air port portion 50 opened to the atmosphere and a sterile filter 52 may be provided at one end of an air introduction path 35. The sterile filter 52 may be configured to hold the connection circuit 24 in a sterile state. The other end of the air introduction path 35 may be connected to a portion between the second connection portion 40 and the first sensor 26 in the sensor flow path 46. Hereinafter, the connection portion between the sensor flow path 46 and the air introduction path 35 may be referred to as a fourth connection portion 54.

A first sensor 26 and a second sensor 28 may be provided in the sensor flow path 46 so as to be in contact with the sample. The first sensor 26 may be an integrally molded product and may include a pH sensor 60 and/or a gas concentration sensor 62. The pH sensor 60 may be configured to measure pH in the sample. The gas concentration sensor 62 may be configured to measure a gas concentration in the sample. Specifically, the gas concentration sensor 62 may include an $O_2$ sensor 64 that measures an $O_2$ concentration in the sample and/or a $CO_2$ sensor 66 that measures a $CO_2$ concentration in the sample.

The second sensor 28 includes, for example, a biosensor such as an enzyme sensor. The second sensor 28 may be provided downstream of the first sensor 26 in the sensor flow path 46. The second sensor 28 may be an integrally molded product and may include a glucose sensor 68 that is configured to measure a glucose concentration in the sample and/or a lactic acid sensor 70 that is configured to measure a lactic acid concentration in the sample. The second sensor 28 is not limited to the enzyme sensor and may include a non-enzyme type glucose sensor. The measurement items of the second sensor 28 are not limited to glucose and lactic acid and may include glutamic acid or the like.

The circuit control device 14 may include a plurality of clamps 72 and one pump 74. In at least one example embodiment, the circuit control device 14 may include, as the plurality of clamps 72, a first clamp 72a (e.g., first opening/closing portion), a second clamp 72b, a third clamp 72c, a fourth clamp 72d (e.g., second opening/closing portion), a fifth clamp 72e, and a sixth clamp 72f (e.g., third opening/closing portion).

The first clamp 72a may be disposed so as to face the first sample introduction path 34a in a state where the sampling kit 12 is attached to the circuit control device 14 (hereinafter, referred to as a "set state") and opens and closes an internal flow path of the first sample introduction path 34a. The second clamp 72b may be disposed so as to face the second sample introduction path 34b in the set state and opens and closes an internal flow path of the second sample introduction path 34b. The third clamp 72c may be disposed so as to face a portion of the sensor flow path 46 between the second sensor 28 and the waste liquid storage portion 22 in the set state and opens and closes an internal flow path of the portion of the sensor flow path 46. The fourth clamp 72d may be disposed so as to face a portion of the introduction path 32 on the upstream side of the third connection portion 48 in the set state and opens and closes an internal flow path of the portion of the introduction path 32. The fifth clamp 72e may be disposed so as to face the standard solution introduction path 33 in the set state and opens and closes an internal flow path of the standard solution introduction path 33. The sixth clamp 72f may be disposed so as to face the air introduction path 35 in the set state and opens and closes an internal flow path of the air introduction path 35.

The pump 74 may be configured to rotate so as to strip off a wall portion constituting a flow path (tube) of the connection circuit 24, thereby applying a flow force to the liquid inside. The pump 74 may be disposed so as to be in contact with a portion of the sensor flow path 46 between the second connection portion 40 and the first sensor 26 in a set state. The pump 74 may be configured to perform first rotation operation (e.g., rotation operation in a direction of an arrow R1) such that a flow force in a direction toward the first sensor 26 (e.g., waste liquid storage portion 22) is applied to the liquid circulating through the sensor flow path 46. The pump 74 may perform second rotational operation (e.g., rotational operation in a direction of an arrow R2) such that a flow force in the direction toward the second connection portion 40 is applied to the liquid circulating through the sensor flow path 46.

The controller 16 (e.g., control unit) may include a computer having a processor, a memory, and/or an input/output interface (not illustrated). The controller 16 may be configured to perform overall control of the entire system by the processor executing a program stored in the memory. The controller 16 may be connected to the circuit control device 14 by communication means including wired, wireless, network, or a combination thereof. Specifically, the controller 16 may be configured to control operation of the plurality of clamps 72 and the pump 74.

Figure 3:
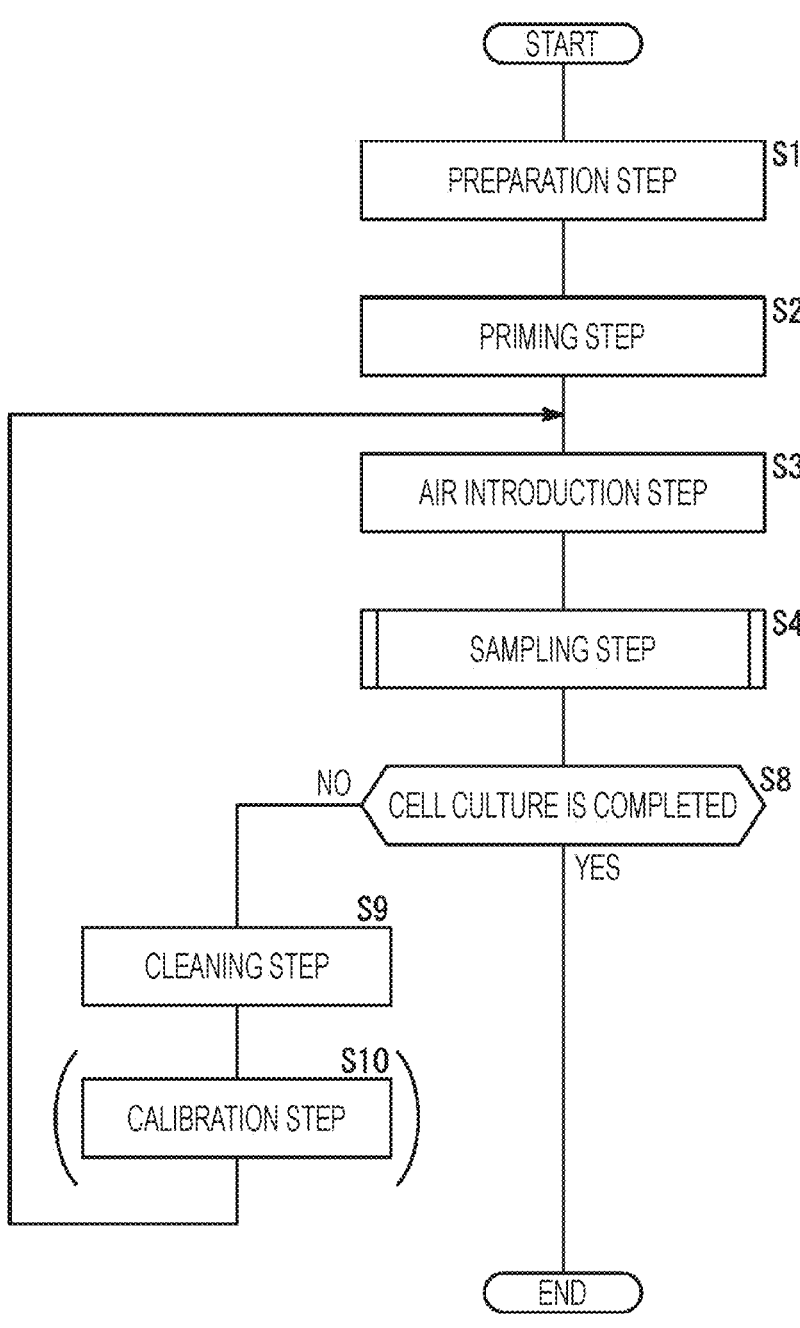
FIG. 3 is a flowchart illustrating a sampling method using the sampling system illustrated in FIG. 1 in accordance with at least one example embodiment of the present disclosure.

In at least one example embodiment, as illustrated in FIG. 3, the sampling method may include a preparation step, a priming step, an air introduction step, a sampling step, a cleaning step, and/or a calibration step.

As illustrated in FIGS. 1 and 2, the preparation step (e.g., step S1 in FIG. 3) may include attaching the sampling kit 12 to the circuit control device 14, connecting the introduction connector 42 of the first sample introduction path 34a to the sampling connector 228 of the first cell culture device 200A, and connecting the introduction connector 42 of the second sample introduction path 34b to the sampling connector 228 of the second cell culture device 200B.

Figure 5:
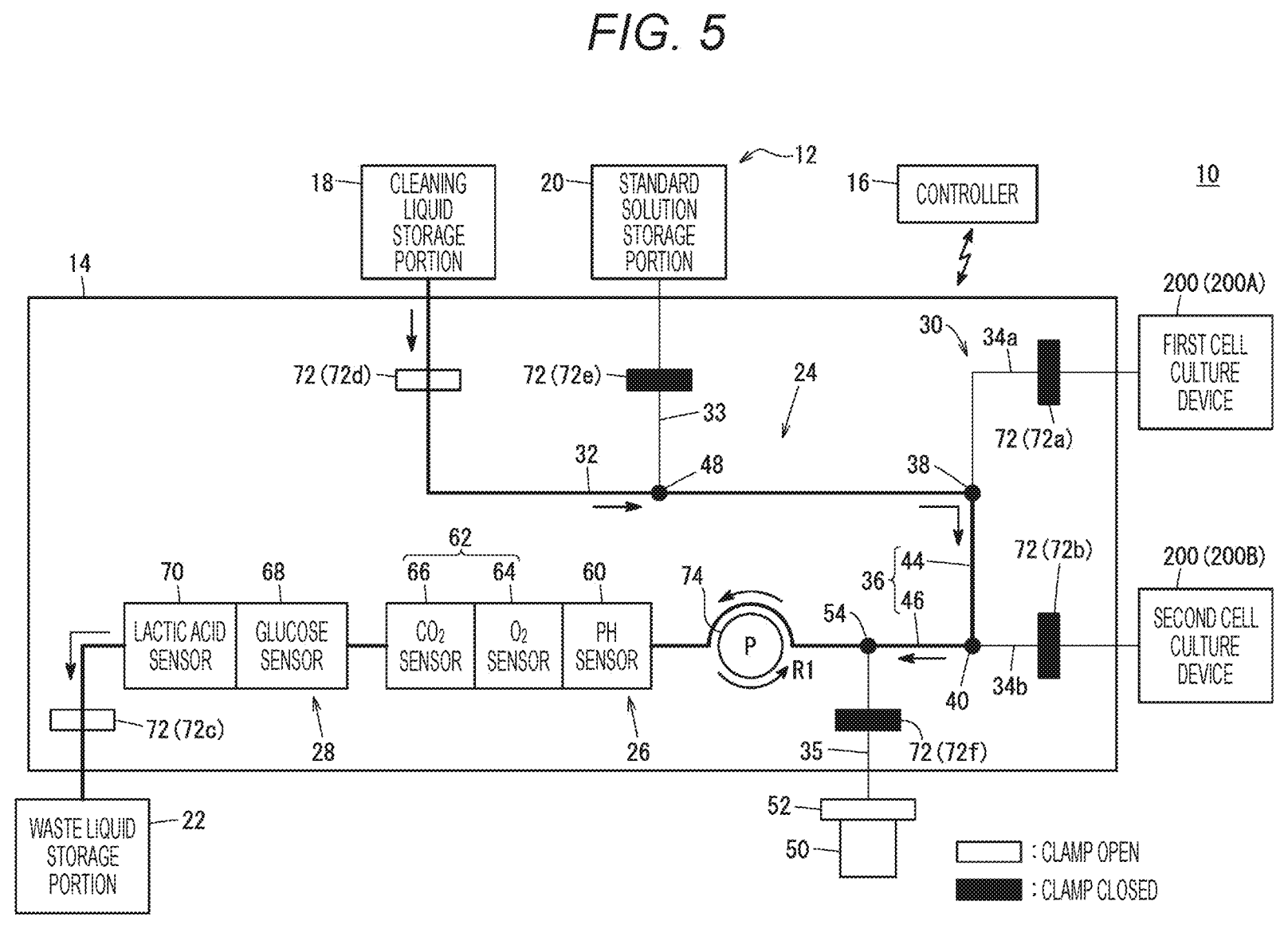

As illustrated in FIG. 5, the priming step (e.g., step S2 in FIG. 3) may include causing, for example using or by the controller 16, the pump 74 to perform the first rotation operation in a state where the third clamp 72c and the fourth clamp 72d are opened and the first clamp 72a, the second clamp 72b, the fifth clamp 72e, and the sixth clamp 72f are closed. Then, the cleaning liquid in the cleaning liquid storage portion 18 may be guided from the introduction path 32 to the waste liquid storage portion 22 via the first connection portion 38, the intermediate flow path 44, the second connection portion 40, and/or the sensor flow path 46 by the action of the pump 74.

Figure 6:
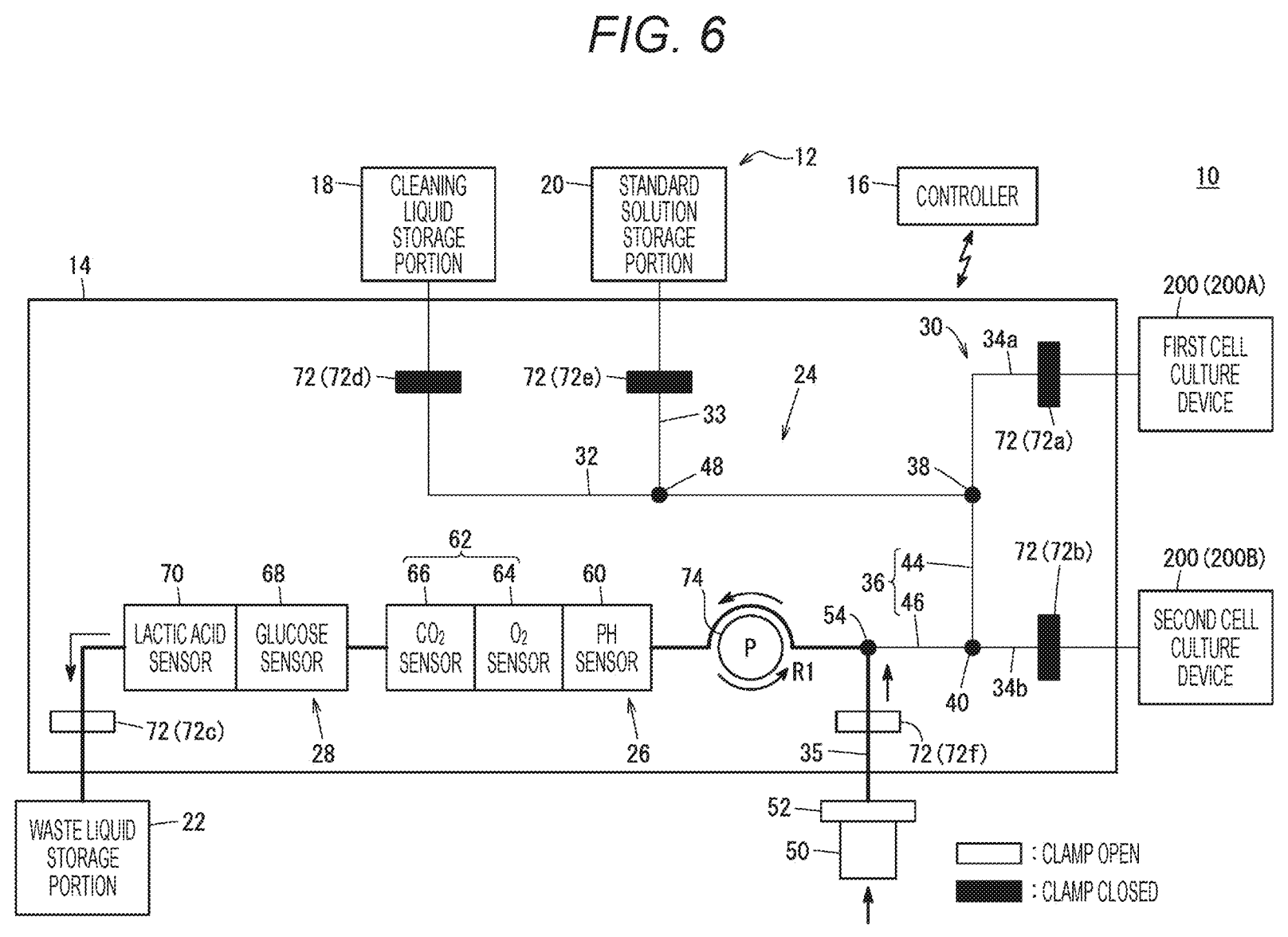

The air introduction step (e.g., step S3 in FIG. 3) may follow the priming step. For example, as illustrated in FIG. 6, the air introduction step may include causing, for example using or by the controller 16, the pump 74 to perform the first rotation operation in a state where the third clamp 72c and the sixth clamp 72f are opened and the first clamp 72a, the second clamp 72b, the fourth clamp 72d, and the fifth clamp 72e are closed. Then, the air introduced from the air port portion 50 to the air introduction path 35 via the sterile filter 52 may be guided to the waste liquid storage portion 22 via the first sensor 26 and the second sensor 28 of the sensor flow path 46. As a result, the cleaning liquid remaining in the first sensor 26 may be pushed out to the waste liquid storage portion 22.

The air introduction step is not limited to an example where the air introduced into the air introduction path 35 is guided to the waste liquid storage portion 22. In the air introduction step, it is sufficient that the cleaning liquid remaining in the gas concentration sensor 62 is replaced with air. In other words, a timing of stopping introduction of air (e.g., stopping driving of the pump 74) in the air introduction step may be a time point at which the air is guided to the portion between the first sensor 26 and the second sensor 28 of the sensor flow path 46.

The sampling step (e.g., step S4 in FIG. 3) may follow the air introduction step. For example, a sample to be collected may be selected (e.g., step S5 in FIG. 4), for exampling using or by the controller 16. In other words, the controller 16 may selects which one of the sample (i.e., first sample) of the first cell culture device 200A and the sample (i.e., second sample) of the second cell culture device 200B is to be collected on the basis of a cell culture state of the cell culture device 200.

Figure 4:
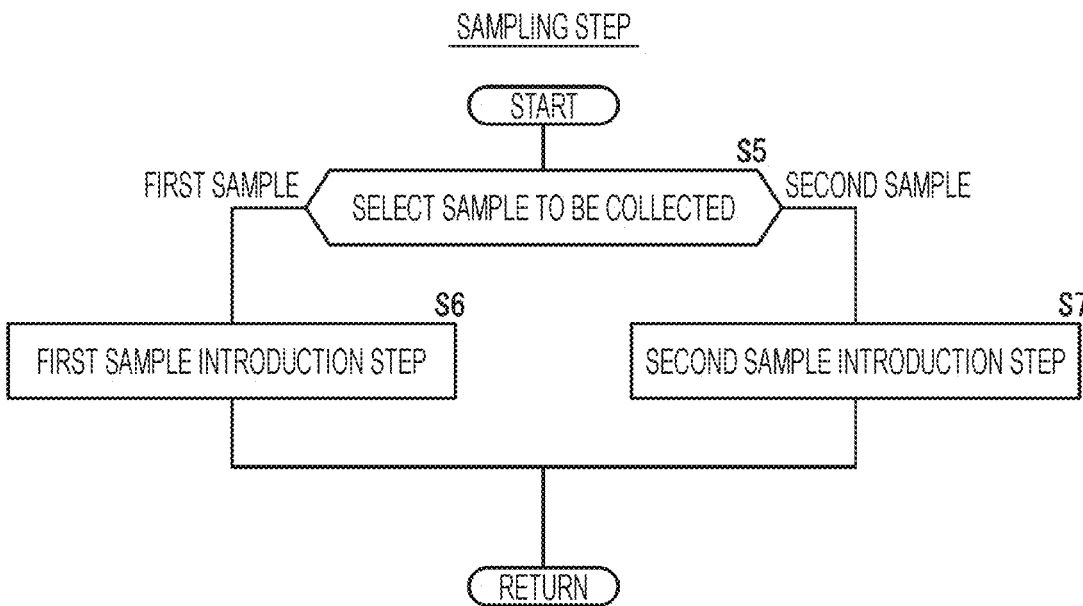
FIG. 4 is a flowchart further illustrating a sampling step of the sampling method illustrated in FIG. 3 in accordance with at least one example embodiment of the present disclosure.
Figure 7:
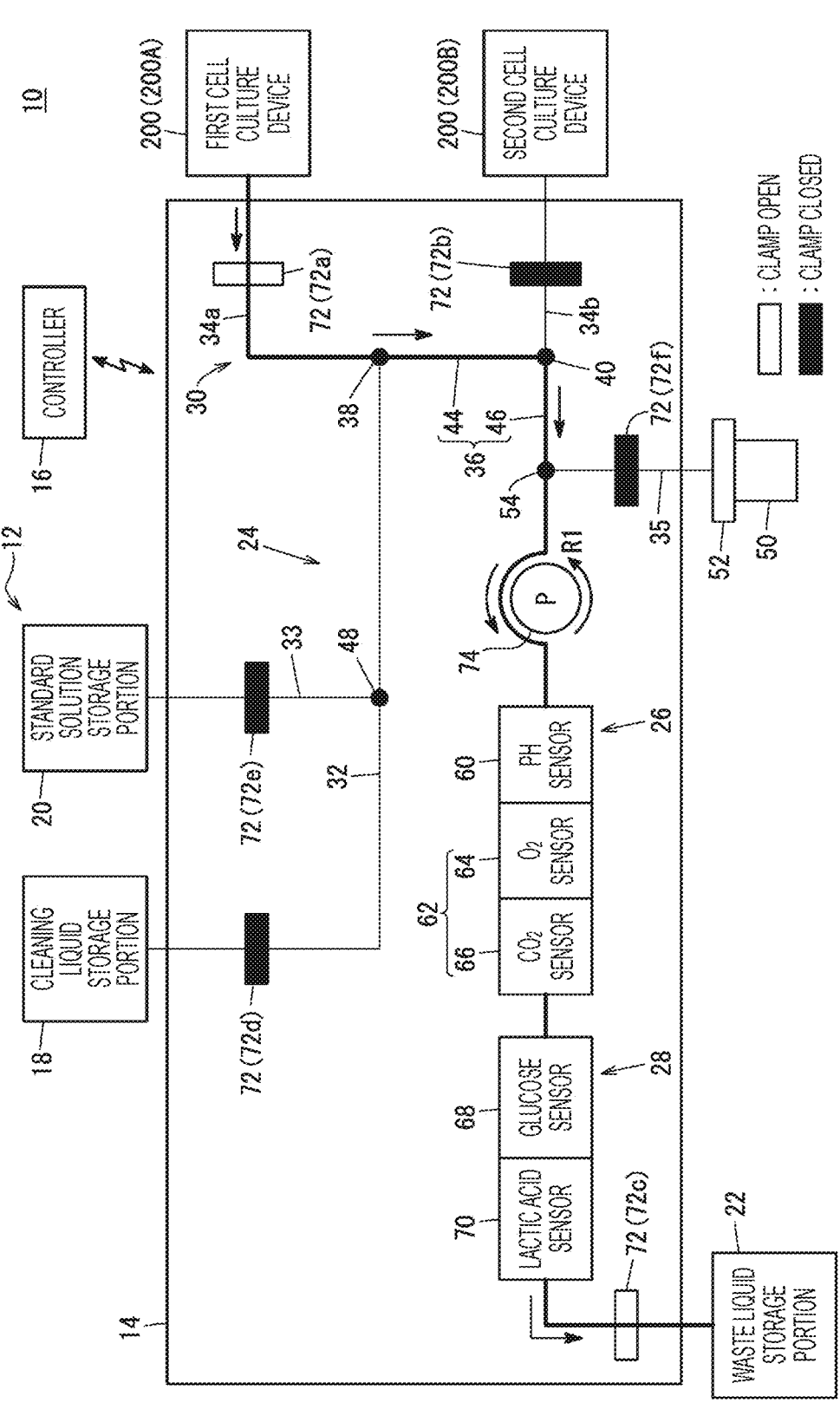
FIG. 7 is a schematic illustrating a third operation of the sampling method illustrated in FIGS. 3 and 4 in accordance with at least one example embodiment of the present disclosure.

When the first sample is selected, the first sample introduction step may be performed (e.g., step S6 in FIG. 4). For example, as illustrated in FIG. 7, the first sample introduction step may include causing, for example using or by the controller 16, the pump 74 to perform the first rotation operation in a state where the first clamp 72a and the third clamp 72c are opened and the second clamp 72b, the fourth clamp 72d, the fifth clamp 72e, and the sixth clamp 72f are closed. Then, the first sample of the first cell culture device 200A may be guided to the waste liquid storage portion 22 via the first sample introduction path 34a, the first connection portion 38, the intermediate flow path 44, the second connection portion 40, and/or the sensor flow path 46 by the action of the pump 74.

The cleaning liquid does not remain in the first sensor 26 (e.g., the cleaning liquid in the first sensor 26 is replaced with air in the air introduction step), and thus, the cleaning liquid is not mixed into the first sample circulating through the first sensor 26.

The first sensor 26 and/or the second sensor 28 may be positioned to be contact with the first sample. The first sensor 26 may be configured to measure the pH, the $O_2$ concentration, and/or the $CO_2$ concentration of the first sample. The measurement results of the first sensor 26 may be transmitted to the controller 16. The second sensor 28 may be configured to measure the glucose concentration and/or the lactic acid concentration of the first sample. The measurement results of the second sensor 28 may be transmitted to the controller 16. The controller 16 may be configured to control culture conditions of the first cell culture device 200A on the basis of the measurement results of the first sensor 26 and/or the second sensor 28.

Figure 8:
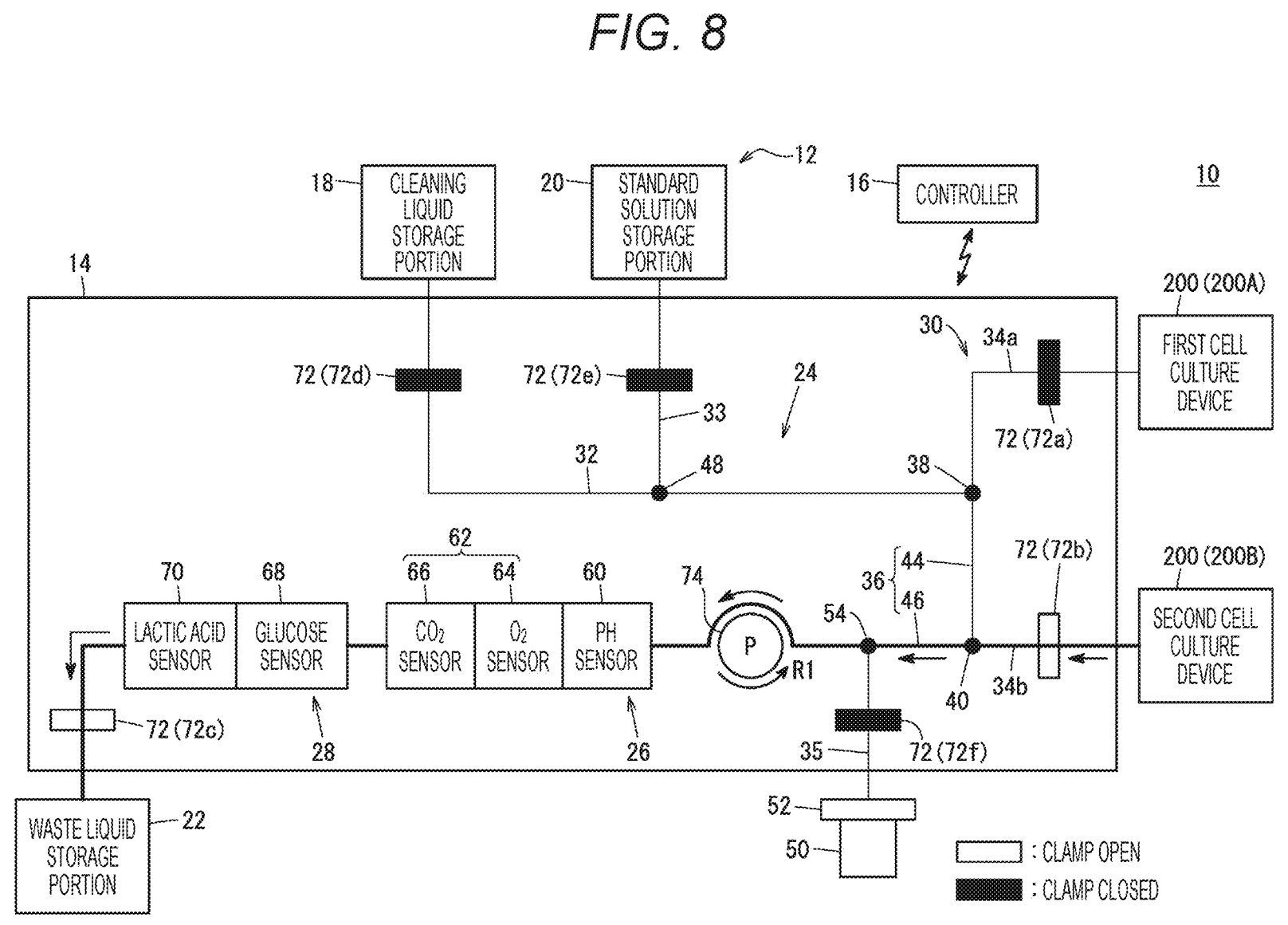

When the controller 16 selects to collect the second sample, the second sample introduction step may be performed (e.g., step S7 in FIG. 4). For example, as illustrated in FIG. 8, the second ample introduction step may include causing, for example using or by the controller 16, the pump 74 to perform the first rotation operation in a state where the second clamp 72b and the third clamp 72c are opened and the first clamp 72a, the fourth clamp 72d, the fifth clamp 72e, and the sixth clamp 72f are closed. Then, the second sample of the second cell culture device 200B may be guided to the waste liquid storage portion 22 via the second sample introduction path 34b, the second connection portion 40, and/or the sensor flow path 46 by the action of the pump 74.

The cleaning liquid does not remain in the first sensor 26 (e.g., the cleaning liquid in the first sensor 26 is replaced with air in the air introduction step), and thus, the cleaning liquid is not mixed into the second sample circulating through the first sensor 26.

The first sensor 26 and/or the second sensor 28 may be positioned to be in contact with the second sample. The first sensor 26 may be configured to measure the pH, the $O_2$ concentration, and/or the $CO_2$ concentration in the second sample. The measurement results of the first sensor 26 may be transmitted to the controller 16. The second sensor 28 may be configured to measure the glucose concentration and/or the lactic acid concentration in the second sample. The measurement results of the second sensor 28 may be transmitted to the controller 16. The controller 16 may be configured to control culture conditions of the second cell culture device 200B on the basis of the measurement results of the first sensor 26 and/or the second sensor 28.

Upon completion of the sampling step, the controller 16 may be configured to determine whether or not the cell culture of the first cell culture device 200A and the second cell culture device 200B has been completed (e.g., step S8 in FIG. 3). In a case where the controller 16 determines that the cell culture has not been completed (e.g., step S8: NO), the cleaning step (e.g., step S9) may be performed. In the cleaning step, for example as illustrated in FIG. 5, the controller 16 may operate the plurality of clamps 72 and the pump 74 similarly to the priming step. Then, the cleaning liquid in the cleaning liquid storage portion 18 may circulate in the first sensor 26 and the second sensor 28 and may be guided to the waste liquid storage portion 22.

As a result, in the first sensor 26, the sample attached to the pH sensor 60, the $O_2$ sensor 64, and/or the $CO_2$ sensor 66 may be removed by the cleaning liquid. In the second sensor 28, the sample attached to the glucose sensor 68 and/or the lactic acid sensor 70 may be removed by the cleaning liquid.

Figure 9:
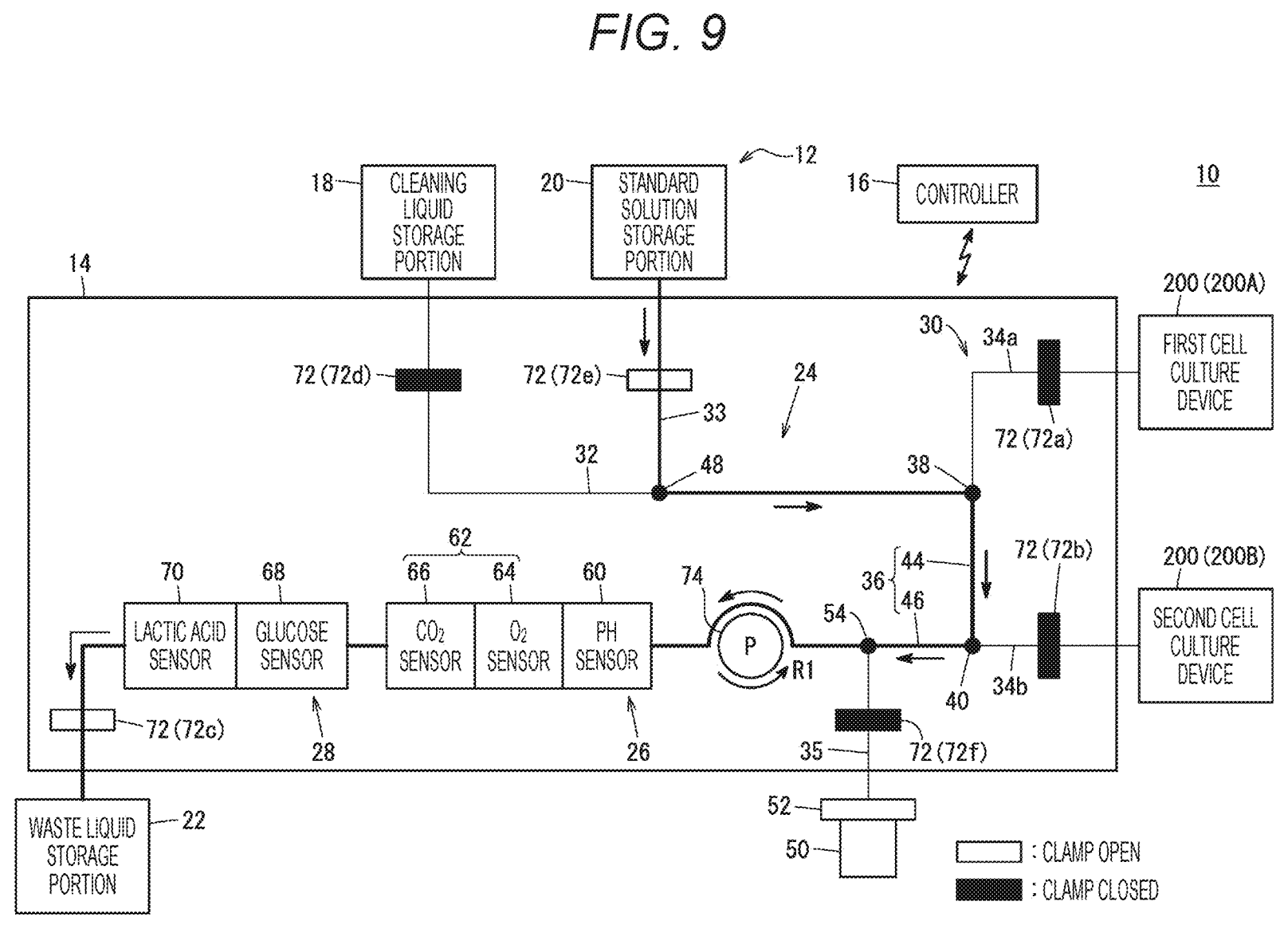

Following the cleaning step (e.g., step S9 in FIG. 3), the calibration step (e.g., step S10 in FIG. 3) may be performed as necessary. As illustrated in FIG. 9, the calibration step may include, for example using or by the controller 16, opening the third clamp 72c and the fifth clamp 72e and causing the pump 74 to perform the first rotation operation in a state where the first clamp 72a, the second clamp 72b, the fourth clamp 72d, and the sixth clamp 72f are closed. Then, the standard solution in the standard solution storage portion 20 may be guided to the waste liquid storage portion 22 via the standard solution introduction path 33, the introduction path 32, the first connection portion 38, the intermediate flow path 44, the second connection portion 40, and/or the sensor flow path 46 by the action of the pump 74.

The first sensor 26 may be configured to measure the pH, the $O_2$ concentration, and/or the $CO_2$ concentration in the standard solution. The measurement results of the first sensor 26 may be transmitted to the controller 16. The controller 16 may be configured to calibrate the pH sensor 60, the $O_2$ sensor 64, and/or the $CO_2$ sensor 66 on the basis of the measurement results of the first sensor 26. The second sensor 28 may be configured to measure the glucose concentration and/or the lactic acid concentration in the standard solution. The measurement results of the second sensor 28 may be transmitted to the controller 16. The controller 16 may be configured to calibrate the glucose sensor 68 and/or the lactic acid sensor 70 on the basis of the measurement results of the second sensor 28. When the calibration step is completed, the steps after step S3 may be sequentially performed. In at least one example embodiment, the sampling step may be performed two or more times.

When it is determined that the cell culture has been completed (e.g., step S8 in FIG. 3: YES), for example using or by the controller 16, a series of operation flow ends.

In at least one example embodiment, the cleaning step may be performed after the sampling step, and thus, the sample attached to the second sensor 28 during the sampling step can be removed by the cleaning liquid in the cleaning step. In the air introduction step, after the cleaning step, the cleaning liquid remaining in the gas concentration sensor 62 may be replaced with air. It is therefore possible to prevent the cleaning liquid from being mixed into the sample inside the gas concentration sensor 62 in sampling steps following the cleaning step, preventing decreases in the measurement accuracy of the gas concentration sensor 62.

The sampling system 10 may include an introduction path 32 that introduces a cleaning liquid into the sampling channel 30 upstream of the second sensor 28, an air introduction path 35 connected to the sampling channel 30 upstream of the gas concentration sensor 62 and opened to the atmosphere, a first clamp 72*a* that is configured to open and close the sampling channel 30 upstream of a first connection portion 38 with the introduction path 32, a fourth clamp 72*d* that is configured to open and close the introduction path 32, a sixth clamp 72*f* that is configured to open and close the air introduction path 35, and a pump 74 provided in the sampling channel 30. In the air introduction step, air may be guided from the air introduction path 35 to the sampling channel 30 by driving the pump 74 in a state where the first clamp 72*a* and the fourth clamp 72*d* are closed and the sixth clamp 72*f* is opened.

The air introduction path 35 may be provided with the sterile filter 52. In the air introduction step, the air that passes through the sterile filter 52 may be guided to the sampling channel 30.

Accordingly, the sample can be held in a sterile state by the sterile filter 52.

The sampling channel 30 may include a sample flow path 36 that includes a second sensor 28 and/or a gas concentration sensor 62 and that forms a downstream side of the first connection portion 38 coupling the introduction path 32 and the sampling channel 30. The sampling channel 30 may also include a first sample introduction path 34*a* that is configured to guide the first sample of the first cell culture device 200A to the first connection portion 38, and a second sample introduction path 34*b* that is configured to guide the second sample of the second cell culture device 200B to an upstream side of the second sensor 28 and/or the gas concentration sensor 62 in the sample flow path 36. The sampling step may include a first sample introduction step of introducing the first sample of the first cell culture device 200A from the first sample introduction path 34*a* into the sample flow path 36, and a second sample introduction step of introducing the second sample of the second cell culture device 200B from the second sample introduction path 34*b* into the sample flow path 36.

Accordingly, it is possible to prevent the cleaning liquid from being mixed into the first sample or the second sample inside the gas concentration sensor 62.

The sampling system 10 may be configured to collect a sample of one cell culture device 200 and measure concentrations of predetermined components. In such instances, the sampling system 10 does not have to include the second sample introduction path 34*b*. In addition, the sampling system 10 may collect samples of three or more cell culture devices 200 individually and measure concentrations of predetermined components. In other words, the number of cell culture devices 200 connected to the sampling channel 30 may be three or more. In such instances, sample introduction paths of the number corresponding to the number of cell culture devices 200 may be provided. The air introduction path 35 may be connected to any one of the intermediate flow path 44, the first sample introduction path 34*a*, the second sample introduction path 34*b*, and/or the introduction path 32.

The present invention is not limited to the embodiments described above and may be modified in various manners without departing from the gist of the present invention. In at least one example embodiment, the cell culture system in which the sampling system 10 and the cell culture device 200 are configured separately is illustrated, but the cell culture system may be one in which the sampling system 10 and the cell culture device 200 are integrated.

In at least one example embodiment, a sampling method includes a sampling step, a cleaning step, and an air introduction step. The sampling method may use a sampling system (10). The sampling system may include a sampling channel (30) that is configured to collect or receive a liquid sample from a cell culture device (200). The sampling channel may include a biosensor (28) and/or a gas concentration sensor (62). The biosensor and/or the gas concentration sensor are provided so as to be in contact with the sample. The sampling step may include circulating the sample from the cell culture device to the sampling channel and measuring concentrations of predetermined components in the sample using the biosensor and/or the gas concentration sensor. The cleaning step may include, after the sampling step, circulating a cleaning liquid through the sampling channel and circulating the cleaning liquid through the biosensor and the gas concentration sensor. The air introduction step may include, after the cleaning step, replacing any cleaning liquid remaining inside the gas concentration sensor with air The sampling step may be performed two or more times. The second and subsequent sampling steps may be performed after the air introduction step.

In at least one example embodiment, the sampling system may also include an introduction path (32) that is configured to introduce the cleaning liquid to an upstream side of the biosensor in the sampling channel; an air introduction path (35) that is connected to the sampling channel upstream of the gas concentration sensor and is opened to the atmosphere; a first opening/closing portion (72*a*) that is configured to open and close an upstream side of a connection portion (38) coupling the introduction path and the sampling channel; a second opening/closing portion (72*d*) that is configured to open and close the introduction path; a third opening/closing portion (72*f*) that is configured to open and close the air introduction path; and a pump (74) provided in the sampling channel, and in the air introduction step, the pump is configured to guide air from the air introduction path to the sampling channel when the first opening/closing portion and the second opening/closing portion are closed and the third opening/closing portion is opened.

In at least one example embodiment, a sterile filter (52) may be provided in the air introduction path, and in the air introduction step, the air that has passed through the sterile filter may be guided to the sampling channel.

In at least one example embodiment, the sampling system may include an introduction path that is configured to introduce the cleaning liquid to the sampling channel upstream of the biosensor. The sampling channel may include a sample flow path (36) provided with the biosensor and/or the gas concentration sensor. The sampling channel may form a downstream side of a connection portion that couples the introduction path and the sampling channel. A first sample introduction path (34*a*) may guide a first sample of a first cell culture device (200A) that is the cell culture device to the connection portion. A second sample introduction path (34*b*) may guide a second sample of a second cell culture device (200B) upstream of the biosensor and/or the gas concentration sensor in the sample flow path. The sampling step may include a first sample introduction step of introducing the first sample of the first cell culture device from the first sample introduction path into the sample flow path and a second sample introduction step of introducing the second sample of the second cell culture device from the second sample introduction path into the sample flow path.

The invention claimed is:

1. A sampling method comprising:
a sampling step that includes
circulating a sample received from a cell culture device to and through a sampling channel of a sampling system, the sampling channel including a biosensor and a gas concentration sensor, the biosensor and the gas concentration sensor each configured to make contact with the sample, and
measuring concentrations of predetermined components in the sample using the biosensor and the gas concentration sensor;
a cleaning step that follows the sampling step, the cleaning step including
circulating a cleaning liquid from a first introduction path of the sampling system through the sampling channel, the cleaning liquid contacting the biosensor and the gas concentration sensor, the first introduction path connecting to the sampling channel upstream of the biosensor and the gas concentration sensor relative to sample flow through the sampling channel; and
an air introduction step that follows the cleaning step, the air introduction step including
replacing any amount of the cleaning liquid remaining in the gas concentration sensor with air from a second introduction path of the sampling system, the second introduction path being separate from the first introduction path, the second introduction path connecting to the sampling channel downstream from a first connection portion that joins the first introduction path and the sampling channel and upstream of the biosensor and the gas concentration sensor relative to sample flow through the sampling channel,
wherein the sampling step is performed two or more times, and the second and subsequent sampling steps are performed after the air introduction step.

2. The sampling method of claim 1, wherein the second introduction path is opened to an atmosphere.

3. The sampling method of claim 2, wherein the second introduction path includes a sterile filter, and in the air introduction step, the air passes through the sterile filter before being guided to the sampling channel.

4. The sampling method of claim 2, wherein the sampling system further includes:
a first clamp configured to open and close the sampling channel upstream of the first connection portion relative to sample flow through the sampling channel;
a second clamp configured to open and close the first introduction path;

a third clamp configured to open and close the second introduction path; and
a pump provided in the sampling channel.

5. The sampling method of claim 4, wherein in the air introduction step, the air is guided from the second introduction path to the sampling channel by driving the pump in a state where the first clamp and the second clamp are closed and the third clamp is opened.

6. The sampling method of claim 1, wherein the sample is a first sample, the cell culture device is a first cell culture device, and the sampling channel further includes:
a sample flow path including the biosensor and the gas concentration sensor downstream of the first connection portion relative to sample flow through the sampling channel;
a first sample introduction path that guides the first sample from the first cell culture device to the sample flow path upstream of both the biosensor and the gas concentration sensor relative to sample flow through the sampling channel and upstream of a second connection portion that joins the second introduction path and the sampling channel relative to sample flow through the sampling channel; and
a second sample introduction path that guides a second sample from a second cell culture device to the sample flow path upstream of both the biosensor and the gas concentration sensor relative to sample flow through the sampling channel and upstream of a second connection portion that joins the second introduction path and the sampling channel relative to sample flow through the sampling channel.

7. The sampling method of claim 6, wherein the circulating of the sample is a first sample introduction step that circulates the first sample received from the first cell culture device to and through the sample flow path, and the sampling step further includes a second sample introduction step that includes circulating a second sample received from the second cell culture device to and through the sample flow path.

8. The sampling method of claim 1, wherein the sampling method further includes:
a calibrating step that includes
circulating a standard solution to and through the sampling channel, the standard solution contacting the biosensor and the gas concentration sensor.

9. The sampling method of claim 8, wherein the standard solution is introduced into the sampling channel from a third introduction path of the sampling sample, the third introduction path connecting to the sampling channel upstream of the biosensor and the gas concentration sensor.

10. A sampling method comprising:
circulating a sample received from a cell culture device to and through a sampling channel of a sampling system, the sampling channel including a biosensor and a gas concentration sensor, the biosensor and the gas concentration sensor each configured to make contact with the sample;
measuring concentrations of predetermined components in the sample using the biosensor and the gas concentration sensor;
after the measuring, circulating a cleaning liquid from a first introduction path of the sampling system through the sampling channel, the cleaning liquid contacting the biosensor and the gas concentration sensor, the first introduction path connecting to the sampling channel upstream of the biosensor and the gas concentration sensor relative to sample flow through the sampling channel; and after the circulation of the cleaning liquid, replacing any amounts of the cleaning liquid remaining in the gas concentration sensor with air from a second introduction path of the sampling sample, the second introduction path being separate from the first introduction path, the second introduction path connecting to the sampling channel downstream from a first connection portion that joins the first introduction path and the sampling channel and upstream of the biosensor and the gas concentration sensor relative to sample flow through the sampling channel.

11. The sampling method of claim 10, wherein the second introduction path is opened to an atmosphere and the replacing of the any amounts of the cleaning liquid remaining in the gas concentration sensor with air includes moving air from the atmosphere into the sampling channel.

12. The sampling method of claim 11, wherein the second introduction path includes a sterile filter, and the replacing of the any amounts of the cleaning liquid remaining in the gas concentration sensor with air includes passing the air through the sterile filter before guiding the air to the sampling channel.

13. The sampling method of claim 11, wherein
the sampling system further includes
a first clamp configured to open and close the sampling channel upstream of the first connection portion relative to sample flow through the sampling channel,
a second clamp configured to open and close the first introduction path,
a third clamp configured to open and close the second introduction path, and
a pump provided in the sampling channel; and
the replacing of the any amounts of the cleaning liquid remaining in the gas concentration sensor with air includes driving the pump in a state where the first clamp and the second clamp are closed, and the third clamp is opened.

14. The sampling method of claim 10, wherein the sample is a first sample, the cell culture device is a first cell culture device, and the sampling channel further includes
a first sample introduction path that guides the first sample from the first cell culture device to the sampling channel upstream of both the biosensor and the gas concentration sensor relative to sample flow through the sampling channel and upstream of a second connection portion that joins the second introduction path and the sampling channel relative to sample flow through the sampling channel; and
a second sample introduction path that guides a second sample from a second cell culture device to the sampling channel upstream of both the biosensor and the gas concentration sensor relative to sample flow through the sampling channel and upstream of a second connection portion that joins the second introduction path and the sampling channel relative to sample flow through the sampling channel.

15. The sampling method of claim 14, wherein the circulating of the sample includes a first sample introduction step that circulates the first sample received from the first cell culture device to and through the sampling channel, and a second sample introduction step that includes circulating a second sample received from the second cell culture device to and through the sampling channel.

16. A sampling method comprising:
receiving a sample from a cell culture device in a sampling channel of a sampling system, the sampling channel including a biosensor and a gas concentration sensor, the biosensor and the gas concentration sensor each configured to make contact with the sample;

measuring concentrations of predetermined components in the sample using the biosensor and the gas concentration sensor;

after the measuring, receiving a cleaning liquid in the sampling channel from a first introduction path of the sampling system, the cleaning liquid contacting the biosensor and the gas concentration sensor, the first introduction path connecting to the sampling channel upstream of the biosensor and the gas concentration sensor relative to sample flow through the sampling channel; and after the receipt of the cleaning liquid, receiving air in the sampling channel from a second introduction path of the sampling system to replace any amounts of the cleaning liquid remaining in the gas concentration sensor, the second introduction path being separate from the first introduction path, the second introduction path connecting to the sampling channel downstream from a first connection portion that joins the first introduction path and the sampling channel and upstream of the biosensor and the gas concentration sensor relative to sample flow through the sampling channel.

17. The sampling method of claim 16, wherein the second introduction path is opened to an atmosphere and the receiving of the air in the sampling channel to replace any amounts of the cleaning liquid remaining in the gas concentration sensor includes guiding air from the atmosphere into the sampling channel.

18. The sampling method of claim 17, wherein the second introduction path includes a sterile filter, and the receiving of the air in the sampling channel to replace any amounts of the cleaning liquid remaining in the gas concentration sensor includes passing the air through the sterile filter before the guiding of the air to the sampling channel.

19. The sampling method of claim 17, wherein
the sampling system further includes
a first clamp configured to open and close the sampling channel upstream of the first connection portion relative to sample flow through the sampling channel,
a second clamp configured to open and close the first introduction path,
a third clamp configured to open and close the second introduction path, and
a pump provided in the sampling channel; and
the receiving of the air in the sampling channel to replace any amounts of the cleaning liquid remaining in the gas concentration sensor includes driving the pump in a state where the first clamp and the second clamp are closed, and the third clamp is opened.

20. The sampling method of claim 16, wherein the sample is a first sample, the cell culture device is a first cell culture device, and the sampling channel further includes:
a first sample introduction path that guides the first sample from the first cell culture device to the sampling channel upstream of both the biosensor and the gas concentration sensor relative to sample flow through the sampling channel; and
a second sample introduction path that guides a second sample from a second cell culture device to the sampling channel upstream of both the biosensor and the gas concentration sensor relative to sample flow through the sampling channel.

* * * * *